US010226620B2

United States Patent
Racz et al.

(10) Patent No.: US 10,226,620 B2
(45) Date of Patent: Mar. 12, 2019

(54) ANCHOR ELEMENTS, MEDICAL DEVICES INCLUDING ONE OR MORE ANCHOR ELEMENTS AND RELATED ASSEMBLIES AND METHODS

(71) Applicant: Custom Medical Applications, Inc., Johnstown, NY (US)

(72) Inventors: N. Sandor Racz, Farmers Branch, TX (US); James Shoemake, Dallas, TX (US)

(73) Assignee: Custom Medical Applications, Inc., Johnstown, NY (US)

( * ) Notice: Subject to any disclaimer, the term of this patent is extended or adjusted under 35 U.S.C. 154(b) by 48 days.

(21) Appl. No.: 15/039,027

(22) PCT Filed: Nov. 25, 2014

(86) PCT No.: PCT/US2014/067500
§ 371 (c)(1),
(2) Date: May 24, 2016

(87) PCT Pub. No.: WO2015/077796
PCT Pub. Date: May 28, 2015

(65) Prior Publication Data
US 2017/0165478 A1    Jun. 15, 2017

Related U.S. Application Data

(60) Provisional application No. 61/908,603, filed on Nov. 25, 2013.

(51) Int. Cl.
*A61N 1/05* (2006.01)
*A61N 1/36* (2006.01)
(Continued)

(52) U.S. Cl.
CPC .......... *A61N 1/0558* (2013.01); *A61B 5/6882* (2013.01); *A61B 17/0401* (2013.01);
(Continued)

(58) Field of Classification Search
CPC ...... A61N 1/0558; A61N 1/057; A61N 1/059; A61N 1/3605
(Continued)

(56) References Cited

U.S. PATENT DOCUMENTS 3,397,699 A   8/1968  Kohl
4,374,527 A   2/1983  Iversen
(Continued)

FOREIGN PATENT DOCUMENTS

EP   0779080   6/1997
FR    779080   3/1935
(Continued)

OTHER PUBLICATIONS

PCT International Search Report dated Mar. 3, 2015, PCT/US2014/067500.
(Continued)

*Primary Examiner* — Carl H Layno
*Assistant Examiner* — Erin M Piateski
(74) *Attorney, Agent, or Firm* — TraskBritt

(57) ABSTRACT

Anchor elements include at least one protrusion configured to extend transversely from a longitudinal axis of the anchor element when the anchor element is in a deployed state. Anchor element assemblies and medical device assemblies may include such anchor elements. Methods of anchoring a medical device within a subject include securing at least a portion of the medical device within a lumen of at least one anchor element and deploying at least one protrusion of the at least one anchor element.

20 Claims, 8 Drawing Sheets

(51) Int. Cl.
  *A61M 25/00* (2006.01)
  *A61M 31/00* (2006.01)
  *A61B 5/00* (2006.01)
  *A61B 17/04* (2006.01)
  *A61B 17/34* (2006.01)
  *A61M 25/04* (2006.01)
  *A61B 17/00* (2006.01)

(52) U.S. Cl.
  CPC ......... *A61B 17/3468* (2013.01); *A61M 25/00* (2013.01); *A61M 25/04* (2013.01); *A61M 31/00* (2013.01); *A61N 1/057* (2013.01); *A61N 1/059* (2013.01); *A61N 1/3605* (2013.01); *A61B 17/3415* (2013.01); *A61B 2017/00986* (2013.01); *A61B 2017/0409* (2013.01); *A61B 2017/0419* (2013.01); *A61B 2017/0427* (2013.01); *A61B 2017/0437* (2013.01); *A61B 2017/0464* (2013.01); *A61N 1/05* (2013.01)

(58) Field of Classification Search
  USPC ........................................................ 607/116
  See application file for complete search history.

(56) References Cited

U.S. PATENT DOCUMENTS

| | | | |
|---|---|---|---|
| 4,406,042 A | 9/1983 | McPhee | |
| 4,419,819 A | 12/1983 | Dickhudt et al. | |
| 4,913,164 A | 4/1990 | Greene et al. | |
| 5,238,007 A | 8/1993 | Giele et al. | |
| 5,344,439 A | 9/1994 | Otten | |
| 5,584,874 A | 12/1996 | Rugland et al. | |
| 6,358,256 B1 | 3/2002 | Reinhardt | |
| 6,473,654 B1 | 10/2002 | Chinn | |
| 6,517,573 B1 | 2/2003 | Pollock et al. | |
| 6,901,287 B2 | 5/2005 | Davis et al. | |
| 7,056,286 B2 | 6/2006 | Ravenscroft et al. | |
| 7,090,661 B2 | 8/2006 | Morris et al. | |
| D531,724 S | 11/2006 | Gessert et al. | |
| 7,270,650 B2 | 9/2007 | Morris et al. | |
| 7,509,169 B2 | 3/2009 | Eigler et al. | |
| 7,517,337 B2 | 4/2009 | Morris et al. | |
| 7,591,970 B2 | 9/2009 | Olson | |
| 7,731,132 B2 | 6/2010 | Raines, Jr. | |
| 7,753,889 B2 | 7/2010 | Rosenberg | |
| 7,811,251 B2 | 10/2010 | Wenchell et al. | |
| 7,890,186 B2 | 2/2011 | Wardle et al. | |
| 8,016,794 B2 | 9/2011 | Rosenberg et al. | |
| 8,016,813 B2 | 9/2011 | Rosenberg et al. | |
| 8,038,653 B2 | 10/2011 | Rosenberg et al. | |
| 8,118,749 B2 | 2/2012 | White et al. | |
| 8,142,401 B2 | 3/2012 | Rosenberg | |
| 8,229,573 B2 | 7/2012 | Chen et al. | |
| 8,235,948 B2 | 8/2012 | Rosenberg et al. | |
| 8,295,948 B2 | 10/2012 | Barker et al. | |
| 8,298,281 B2 | 10/2012 | Majercak et al. | |
| 8,311,643 B2 | 11/2012 | North | |
| 8,333,687 B2 * | 12/2012 | Farnan ................ A61M 1/3653 600/16 |
| 8,740,972 B2 | 6/2014 | Roeder et al. | |
| D709,753 S | 7/2014 | Guala | |
| D718,436 S | 11/2014 | Redol | |
| D785,793 S | 5/2017 | Landanger | |
| 10,105,224 B2 | 10/2018 | Buchbinder et al. | |
| 2001/0037141 A1* | 11/2001 | Yee ......................... A61F 2/95 623/1.11 |
| 2002/0161341 A1* | 10/2002 | Stinson .................... A61F 2/90 604/264 |
| 2003/0199961 A1* | 10/2003 | Bjorklund ............. A61N 1/057 607/126 |
| 2005/0065589 A1 | 3/2005 | Schneider et al. | |
| 2005/0288604 A1 | 12/2005 | Eigler et al. | |
| 2008/0172118 A1 | 7/2008 | Johnson et al. | |
| 2008/0183257 A1 | 7/2008 | Imran et al. | |
| 2009/0248054 A1* | 10/2009 | Sage .................... A61M 25/02 606/174 |
| 2010/0030311 A1 | 2/2010 | Lazeroms et al. | |
| 2010/0125249 A1* | 5/2010 | Rosenberg ........ A61M 25/0097 604/175 |
| 2010/0174296 A1 | 7/2010 | Vakharia et al. | |
| 2012/0071833 A1 | 3/2012 | Hill et al. | |
| 2012/0083742 A1 | 4/2012 | Nelson | |
| 2014/0188165 A1 | 7/2014 | Sengun et al. | |
| 2014/0276418 A1 | 9/2014 | Nelson et al. | |

FOREIGN PATENT DOCUMENTS

| | | |
|---|---|---|
| FR | 2742058 | 6/1997 |
| JP | 2010516436 A | 5/2010 |
| JP | 2011500286 A | 1/2011 |
| WO | 2010085456 | 7/2010 |
| WO | 2013070490 A1 | 5/2013 |
| WO | 2015077796 | 5/2015 |

OTHER PUBLICATIONS

PCT Written Opinion dated Mar. 3, 2015, PCT/US2014/067500.
Reasons for Refusal in Japanese Patent Application No. 2016-554835 dated Apr. 2, 2018 (14 pages with Translation).
Search Report in Japanese Patent Application No. 2016-554835 dated Mar. 30, 2018 (61 pages with Translation).
Search Report in European Patent Application No. 14863371.2 dated Jul. 27, 2017 (7 pages).
Non-Final Rejection dated Dec 7, 2018 for U.S. Appl. No. 29584674.

\* cited by examiner

ANCHOR ELEMENTS, MEDICAL DEVICES INCLUDING ONE OR MORE ANCHOR ELEMENTS AND RELATED ASSEMBLIES AND METHODS

CROSS-REFERENCE TO RELATED APPLICATIONS

This application is a national phase entry under 35 U.S.C. § 371 of International Patent Application PCT/US2014/067500, filed Nov. 25, 2014, designating the United States of America and published in English as International Patent Publication WO 2015/077796 A1 on May 28, 2015, which claims the benefit under Article 8 of the Patent Cooperation Treaty to U.S. Provisional Patent Application Ser. No. 61/908,603, filed Nov. 25, 2013, for "ANCHOR ELEMENTS, MEDICAL DEVICES INCLUDING ONE OR MORE ANCHOR ELEMENTS AND RELATED ASSEMBLIES AND METHODS," the disclosure of each of which is hereby incorporated herein in its entirety by this reference.

TECHNICAL FIELD

The disclosure relates generally to the field of medical devices and related methods. In particular, the disclosure relates to anchor elements and anchor element assemblies that may be utilized to retain at least a portion of a medical device (e.g., a medical therapy delivery device) within a subject and related methods.

BACKGROUND

Implantable medical devices (e.g., medical therapy delivery devices), such as catheters and leads, may be employed for a variety of therapeutic and diagnostic purposes. Controlled placement and retention of such therapy delivery elements within a subject is highly desirable as precise placement and retention may result in improved therapeutic efficacy or reduced side effects. However, the location of the delivery element may change in time. For example, as the subject moves, the location of the implanted delivery element may move or shift within the subject.

Anchors may be placed about the therapy delivery element and sutured to subcutaneous tissue of the subject in order to secure the position of a delivery region of the therapy delivery element (e.g., an infusion section or electrode of the delivery element) relative to a target location of the subject.

BRIEF SUMMARY

Described are anchor elements, anchor element assemblies, and methods of anchoring at least a portion of a medical device within a subject. Such anchor elements may be positioned and/or deployed within the subject while the at least a portion of the medical device is positioned within (e.g., resident in) a subject. For example, such anchor elements may be positioned and/or deployed within the subject with an anchor deployment device of an anchor element assembly.

In some embodiments, an anchor element assembly comprises at least one anchor element having a longitudinal axis. This anchor element includes at least one lobe section comprising at least one lobe configured to extend transversely or laterally from the longitudinal axis of the at least one anchor element when the anchor element is in a deployed state and a lumen formed within the at least one anchor element configured to receive at least a portion of a medical device in the lumen. The anchor element assembly further comprises an anchor deployment device comprising at least one cannula configured to receive the at least one anchor element on the at least one cannula. The anchor deployment device is configured to secure the anchor deployment device to the at least a portion of the medical device.

In certain embodiments, an anchor element comprising at least one protrusion section comprises at least two circumferentially-spaced protrusions configured to extend transversely or laterally from a longitudinal axis of the anchor element when the anchor element is in a deployed state and a lumen formed within the at least one anchor element configured to receive at least a portion of a medical device in the lumen. The anchor element is configured to be secured over the at least a portion of the medical device while the at least a portion of the medical device is positioned within a subject.

Also disclosed is a method of anchoring a medical device within a subject. The method includes positioning at least a portion of the medical device within the subject, securing the at least a portion of the medical device within a lumen of the at least one anchor element, and deploying at least one protrusion of the at least one anchor element to extend transversely or laterally from a longitudinal axis of the at least one anchor element while the at least a portion of the medical device is positioned within the subject.

Also disclosed are medical device assemblies including such anchor elements and/or anchor element assemblies.

Also disclosed are methods of forming and utilizing anchor elements and anchor element assemblies according to the disclosure.

DETAILED DESCRIPTION

Illustrations presented herein are not necessarily meant to be actual views of any particular device, assembly, system, method, or components thereof, but are merely idealized representations, which are employed to describe embodiments of the disclosure. Additionally, elements common between figures may retain the same numerical designation.

Figure 1:
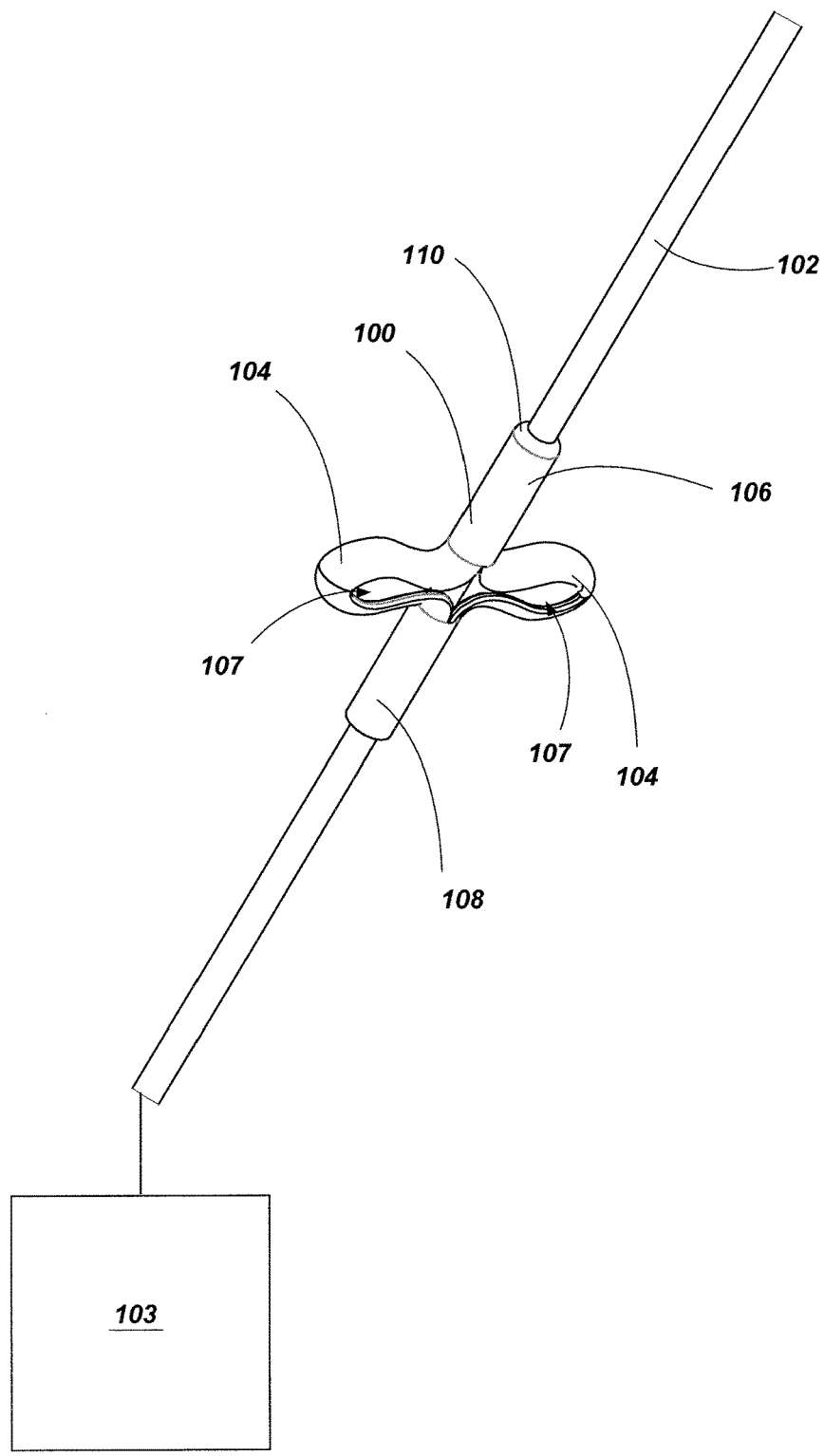
FIG. 1 depicts a medical device assembly including an anchor element positioned on a medical device in accordance with an embodiment of the disclosure.

FIG. 1 depicts a medical device assembly including an anchor element 100 positioned on a medical device 102 (e.g., a distal portion of the medical device 102). Such medical devices 102 may include a diagnostic device, a monitoring device, a therapeutic device, or combinations thereof. For example, the medical device 102 may comprise a medical therapy delivery device, a medical device configured to sense a parameter of the subject, a medical device configured to diagnose a condition, a medical device configured to sample one or more tissues and/or fluids from a subject, or combinations thereof.

The medical device 102 may be utilized alone to provide a medical service (e.g., diagnostic, monitoring, therapeutic, or combinations thereof) to a subject or may be utilized with one or more medical devices 103 (e.g., a medical device internal or external to the subject that is electrically and/or mechanically coupled to the medical device 102). For example, the medical device 102 and/or device 103 may comprise devices such as a pacemaker, defibrillator, monitoring device, infusion device, neurostimulator, gastric stimulator, cochlear device, or any other device that is at least partially subcutaneously implanted in a subject.

In some embodiments, at least a portion of the medical device 102 is positioned proximate the nervous system of a subject (e.g., proximate the spinal cord or canal, brain, and/or peripheral nervous system). The medical device 102 may be a catheter, a lead, or lead extension. For example, the medical device 102 may be a lead including one or more electrodes on a distal end portion of the lead. Electrical contacts in the lead may be electrically coupled (e.g., physically or wirelessly) to a control module having an electrical signal generator (e.g., medical device 103 external or internal to the subject) and signals generated by the medical device 103 may be delivered to the subject via the electrodes. In some embodiments, such leads are utilized as implantable stimulation devices, which may be utilized in a variety of treatments and procedures, such as, for example, spinal cord stimulation. For example, implantable stimulation devices may be used to stimulate nerves, such as the spinal cord, muscles, or other tissue. The stimulator electrodes of the leads may be implanted in contact with or near the nerves, muscles, or other tissue to be stimulated. A pulse generator of the medical device 103 generates electrical pulses that are delivered by the electrodes to body tissue. In such embodiments, the lead is anchored at one or more places in the subject to prevent or reduce movement of the lead or stimulator electrodes within the subject (e.g., during short-term or long-term placement of the devices 102, 103 in the subject) that could damage tissue, move the stimulator electrodes out of the desired position, or interrupt the connection between the stimulator electrodes and the medical device 102, 103.

As shown in FIG. 1, the anchor element 100 is placed over at least a portion of the medical device 102 (e.g., a cannula of the medical device 102). For example, at least a portion of the medical device 102 may be positioned within a lumen formed by the tubular body (e.g., cannula) of the anchor element 100. As depicted, the anchor element 100 is shown in a deployed state where one or more protrusions (e.g., one, two, three, four, or more lobes 104, e.g., circumferentially-spaced lobes) extend outwardly from a portion of the anchor element 100 (e.g., laterally outward from a longitudinal axis or centerline of the anchor element 100). Each lobe 104 extending laterally from the anchor element 100 may form an opening 107 within the lobe 104.

When attached to the medical device 102, the lobes 104 of the anchor element 100 may anchor the medical device 102 by engaging with one or more portions of the subject. For example, the lobes 104 of the anchor element 100 may engage with a portion of the subject's tissue (e.g., muscle tissue, nervous tissue, connective tissue, etc.) to at least partially retain the medical device 102 in a desired position within the subject. It is also believed that, in some embodiments, regrowth of the tissue of the subject proximate the lobes 104 may intertwine with at least a portion of the lobes 104 (e.g., tissue may extend through the openings 107) further anchoring the anchor element 100 and medical device 102 within the subject.

The anchor element 100 may be coupled (e.g., mechanically coupled) to at least a portion of the medical device 102 (e.g., an outer portion or exterior surface of the medical device 102). For example, the anchor element 100 may be secured to the medical device 102 through mechanical interference (e.g., utilizing friction, compression, swaging, etc.) rather than through adhesion or the use of fasteners. The anchor element 100 may include one or more portions for retaining the anchor element 100 to the medical device 102. For example, engagement portions 106, 108 may be formed on either side of the lobes 104 and may act to secure the anchor element 100 to the medical device 102 (e.g., via a mechanical interference fit). In some embodiments, each of the engagement portions 106, 108 of the anchor element 100 include an inner dimension (e.g., diameter) that is smaller than an outer dimension (e.g., diameter) of the medical device 102. One or more portions of the anchor element 100 (e.g., engagement portions 106, 108) may be formed from a flexible material (e.g., an elastically deformable material) such as, for example, a polymer (e.g., silicone, polyurethane, etc.). The flexible engagement portions 106, 108 may be deformed (e.g., elastically deformed) to enlarge a cross-sectional area of a lumen formed within each the engagement portions 106, 108. The enlarged engagement portions 106, 108 may be positioned over (e.g., around, about) the medical device 102. As the enlarged engagement portions 106, 108 are allowed to contract back to substantially their original size (e.g., cross-sectional area), the engagement portions 106, 108 may engage and couple with the medical device 102.

In some embodiments, one or more ends of the anchor element 100 include a taper 110 or chamfer to assist in insertion of the anchor element 100 into the subject.

Figure 2A:
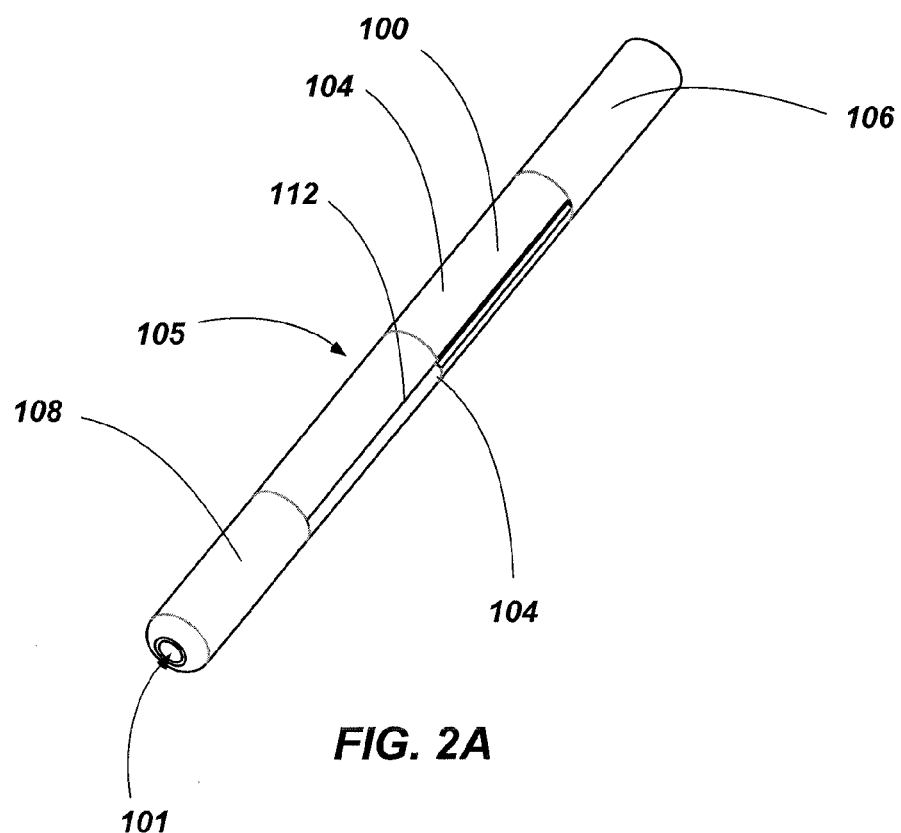
FIGS. 2A and 2B depict an anchor element in accordance with an embodiment hereof in an initial state and a deployed state, respectively.
Figure 2B:
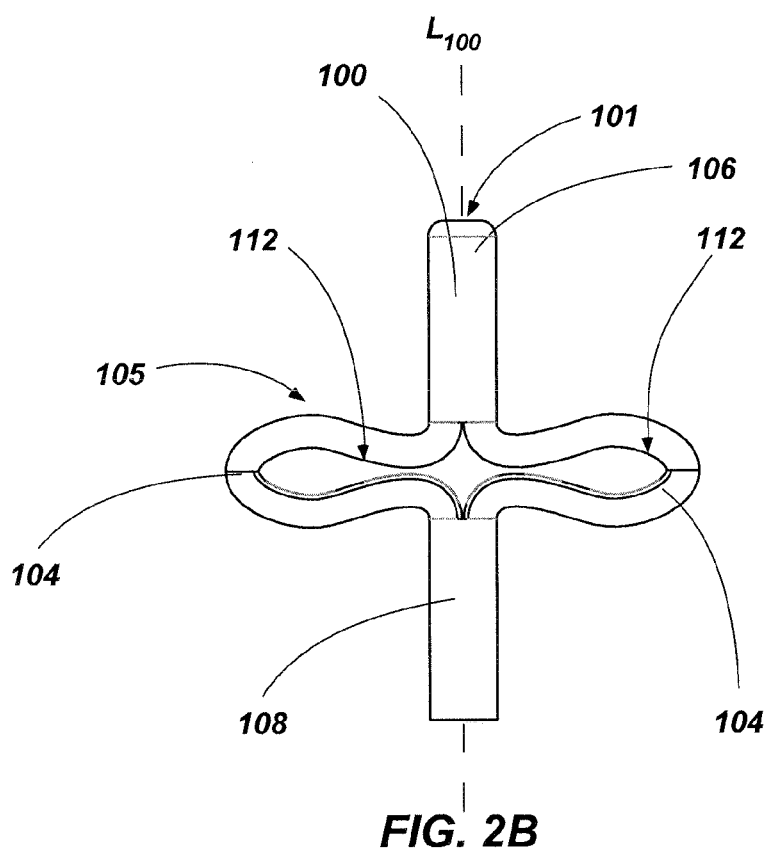

FIGS. 2A and 2B depict an anchor element (e.g., anchor element 100) in an initial state (e.g., a retracted or relaxed state) and a deployed state (e.g., a semi-distended state of the inner diameter), respectively. As shown in FIG. 2A, the anchor element 100 includes a protrusion or lobe portion 105 positioned between the engagement portions 106, 108 of the anchor element 100. The body of the anchor element may form a lumen 101 therein. The lobes 104 (e.g., two lobes 104) of the lobe portion 105 are formed about the anchor element 100 (e.g., at equal circumferential spacing) by slits 112 in the tubular body of the anchor element 100. In the initial state, the lobe portion 105 of the anchor element 100 is substantially parallel to (e.g., coextensive with) a longitudinal axis $L_{100}$ of the anchor element 100.

Referring also to FIG. 2B, the engagement portions 106, 108 may be moved toward each other to transition the anchor element 100 to the deployed state. The slits 112 enable the lobes 104 to extend outwardly (e.g., in a direction lateral or transverse (e.g., perpendicular) to the longitudinal axis $L_{100}$ of the anchor element 100) from a portion of the anchor element 100 (e.g., from the engagement portions 106, 108).

Figure 3A:
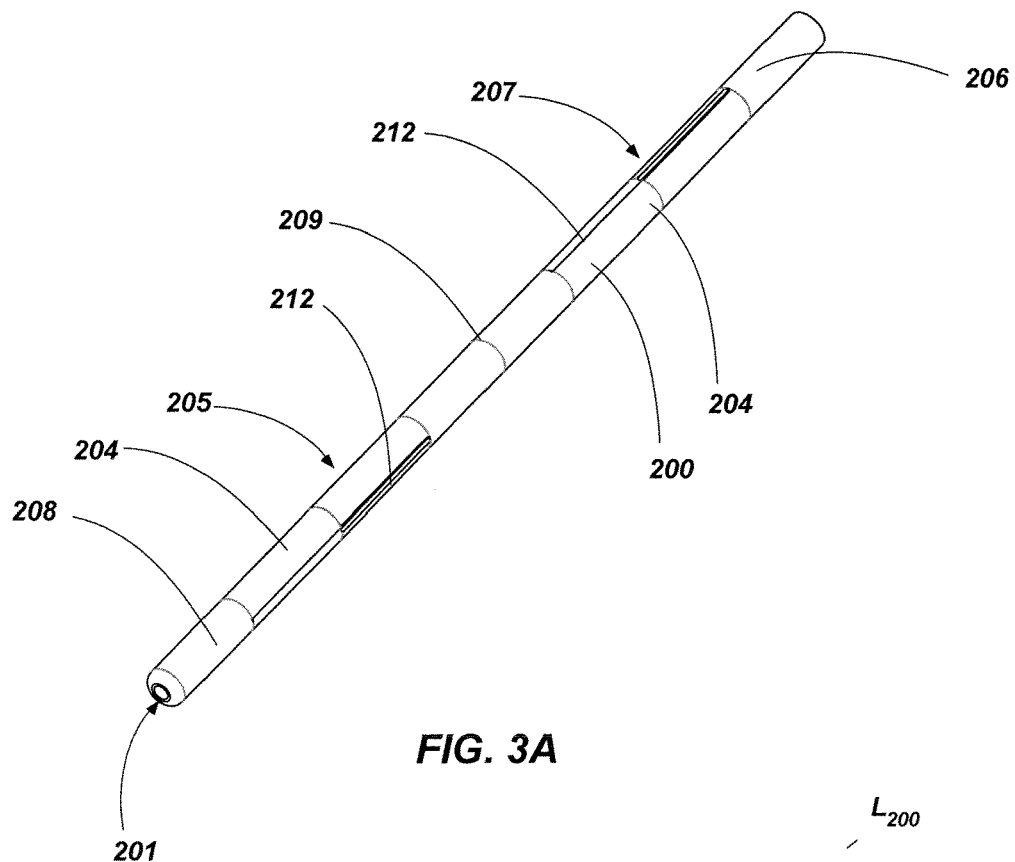
FIGS. 3A and 3B depict an anchor element in accordance with an embodiment hereof in an initial state and a deployed state, respectively.
Figure 3B:
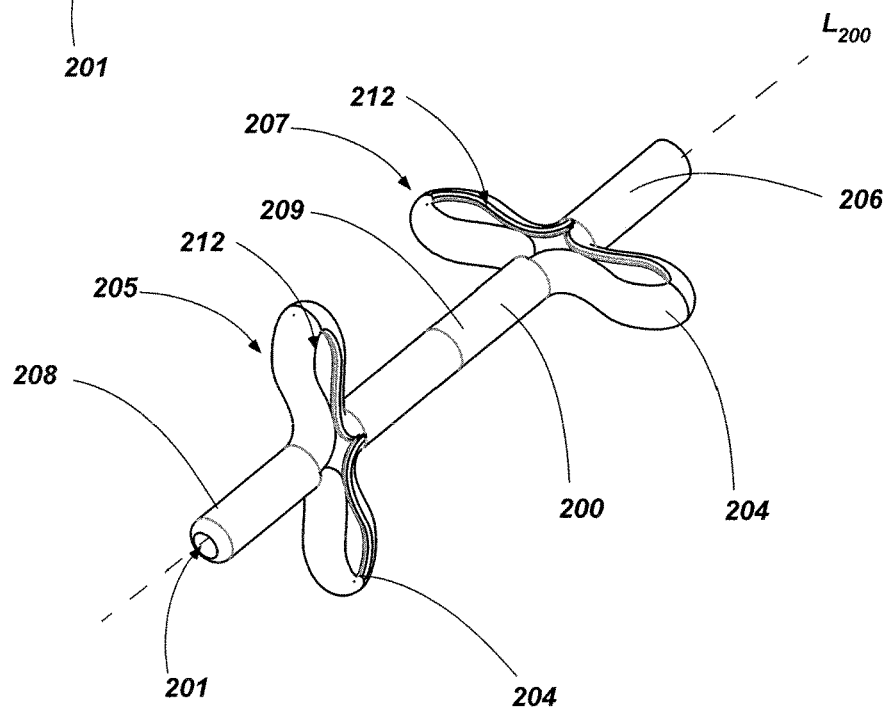

FIGS. 3A and 3B depict an anchor element 200 in an initial state (e.g., a retracted state) and a deployed state, respectively. As shown in FIG. 3A, the anchor element 200 may be somewhat similar to anchor element 100 discussed above and the body of the anchor element 200 may form a lumen 201 therein. However, anchor element 200 may include more than one lobe portion (e.g., two lobe portions 205, 207) positioned between the engagement portions 206, 208 of the anchor element 200. In other embodiments, the anchor element 200 includes three, four, or more lobe portions. Lobes 204 (e.g., two lobes) of each lobe portion 205, 207 are formed about the anchor element 200 (e.g., at equal circumferential spacing) by slits 212 in the tubular body of the anchor element 200. In the initial state, the lobe portions 205 of the anchor element 200 are substantially parallel to (e.g., coextensive with) a longitudinal axis $L_{200}$ of the anchor element 200.

In some embodiments, the anchor element 200 includes an additional engagement portion 209 positioned between the lobe portions 205, 207.

Referring also to FIG. 3B, the engagement portions 206, 208 may be moved toward each other (e.g., toward the additional engagement portion 209) to transition the anchor element 200 to the deployed state. The slits 212 enable the lobes 204 to extend outwardly (e.g., in a direction lateral or transverse (e.g., perpendicular) to a longitudinal axis $L_{200}$ of the anchor element 200) from a portion of the anchor element 200 (e.g., from the engagement portions 206, 208). As depicted, the lobe portions 205, 207 may be offset from one another (e.g., offset 90 degrees about the longitudinal axis $L_{200}$ of the anchor element 200).

Figure 4:
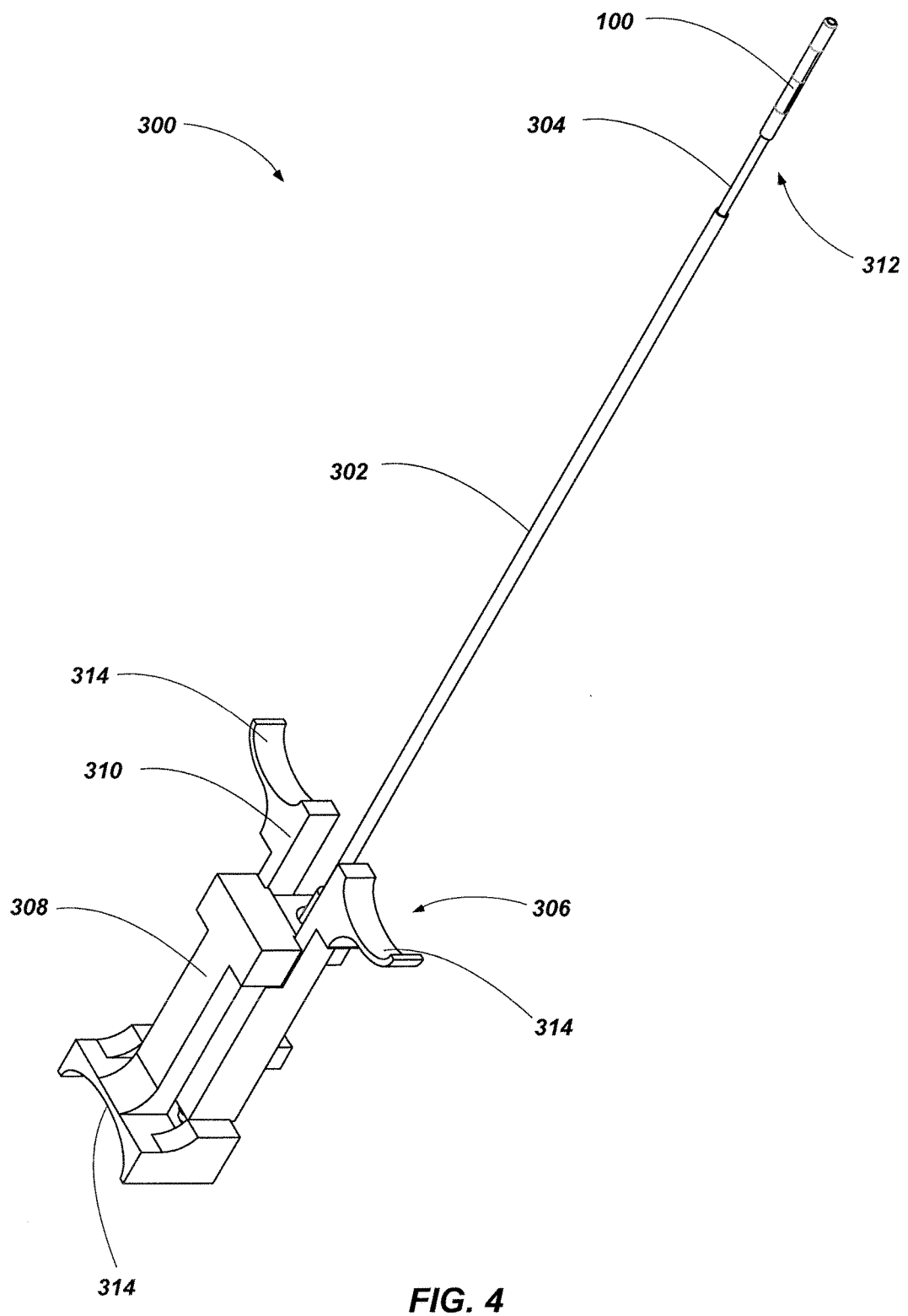
FIG. 4 depicts an anchor deployment device in accordance with one embodiment.

FIG. 4 depicts an anchor deployment device 300 that may be utilized with an anchor element (e.g., anchor elements 100, 200 discussed above with reference to FIGS. 1 through 3B). As shown in FIG. 4, the anchor deployment device 300 includes a first cannula (e.g., deployment cannula 302) and a second cannula (e.g., anchor cannula 304) received at least partially within the deployment cannula 302. For example, the deployment cannula 302 may have an inner dimension (e.g., diameter) that is greater than an outer dimension (e.g., diameter) of the anchor cannula 304 such that the anchor cannula 304 may be received and movable within the deployment cannula 302. The anchor deployment device 300 may include a handle 306 having a first portion 308 coupled to the deployment cannula 302 and a second portion 310 coupled to the anchor cannula 304. The portions 308, 310 of the handle 306 may be movable relative to one another (e.g., the second portion 310 may slide relative to the first portion 308) in order to move the anchor cannula 304 within the deployment cannula 302. Each portion 308, 310 of the handle 306 may include one or more grips 314 enabling a user (e.g., medical practitioner) to actuate the handle 306, thereby sliding the second portion 310 relative to the first portion 308 along a common axis.

As depicted, the anchor cannula 304 may be sized to receive an anchor element (e.g., anchor element 100) on the anchor cannula 304 at distal portion 312 of the anchor deployment device 300. The outer dimension (e.g., diameter) of the anchor cannula 304 may be greater than the inner dimension (e.g., diameter) of the anchor element 100. Such a diameter of the anchor cannula 304 may act to enlarge a cross-sectional area of a lumen 101 formed within a portion of the anchor element 100 (e.g., at each of the engagement portions 106, 108 (FIG. 1)) to form an initial dimension to an enlarged dimension. For example, the anchor cannula 304 may deform (e.g., elastically deform) the anchor element 100 to a dimension (e.g., diameter) that is greater than a dimension (e.g., diameter) of the medical device 102 (FIG. 1) on which the anchor element 100 is to be placed.

Figure 5:
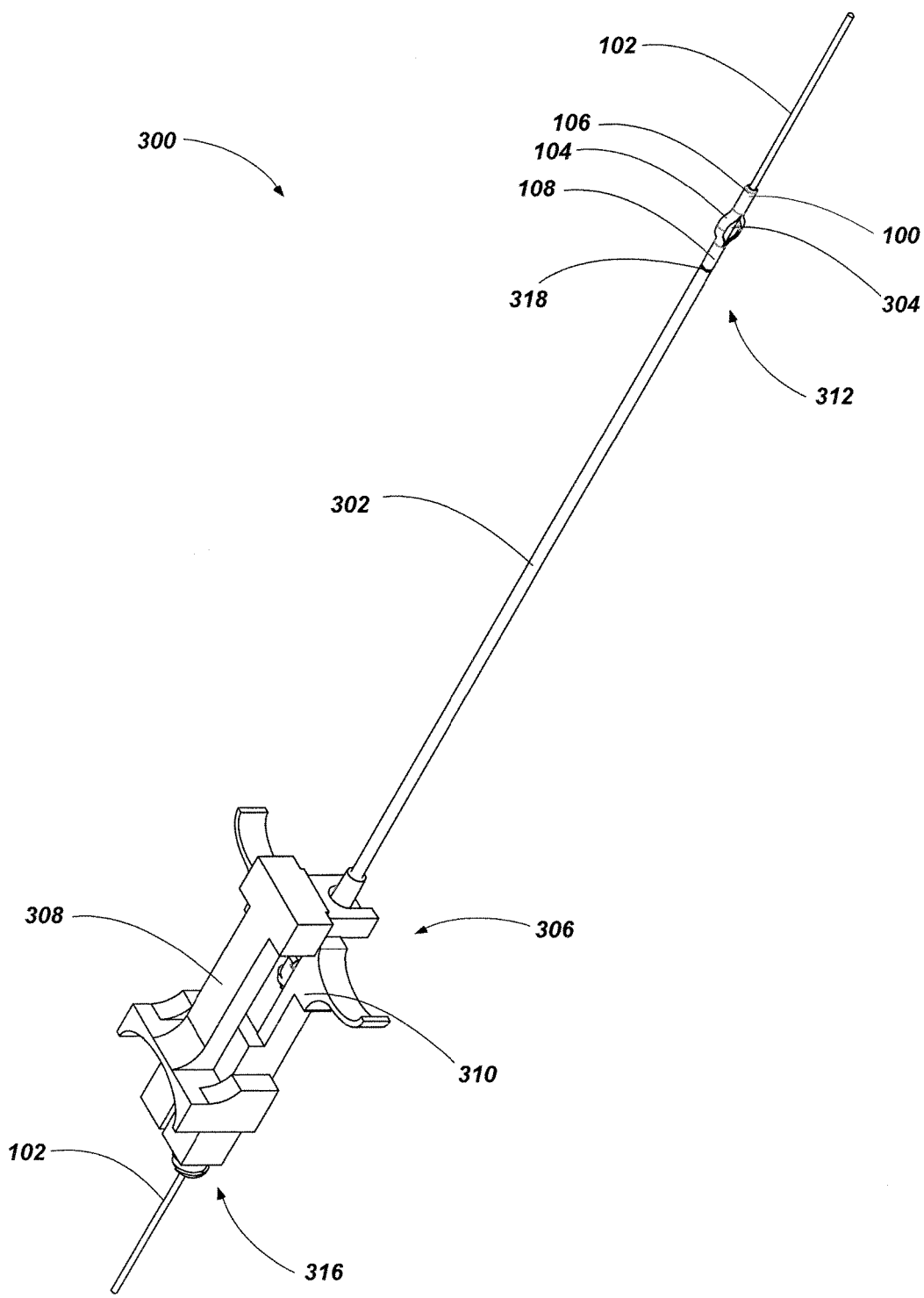
FIG. 5 depicts a view of the anchor deployment device shown in FIG. 4 beginning to deploy an anchor element.

FIG. 5 depicts a view of the anchor deployment device 300 shown in FIG. 4 beginning to deploy an anchor element (e.g., anchor element 100 in a distended state of the inner diameter). As shown in FIG. 5, at least a portion of a medical device (e.g., medical device 102) may be received within a portion of the anchor deployment device 300. For example, the anchor cannula 304 may have an inner dimension (e.g., diameter) that is sized to enable at least a portion of the medical device 102 to be received within the anchor cannula 304. In some embodiments, a proximal portion 316 of the anchor deployment device 300 is configured such that the medical device 102 extends through the anchor deployment device 300 and out of the of the anchor deployment device 300 at the proximal portion 316. Such a configuration may enable a user to position the anchor deployment device 300 along and through the medical device 102 in order to secure an anchor element 100 to the anchor deployment device 300 at any desired position. For example, the medical device 102 may be placed within a subject and the anchor deployment device 300 may be slid along the medical device 102. A portion of the anchor deployment device 300 (e.g., the distal portion 312) may be inserted within the subject to secure the anchor element 100 within the subject while the medical device 102 resides within the subject.

Actuation of the handle 306 may bring the anchor element 100, which is positioned on the anchor cannula 304 (e.g., in a radially enlarged or stretched state), into contact with the deployment cannula 302 (e.g., a leading end 318 of the deployment cannula 302). The deployment cannula 302 may act to force (e.g., slide) at least a portion of the anchor element 100 along the anchor cannula 304. For example, the deployment cannula 302 may force the first engagement portion 106 toward the second engagement portion 108, thereby deploying the lobes 104 of the anchor element 100. As the anchor cannula 304 is slid within the deployment cannula 302, the leading end 318 of the deployment cannula 302 may force the anchor element 100 off of the anchor cannula 304 and onto the medical device 102 (e.g., into the position shown in FIG. 1).

Figure 6:
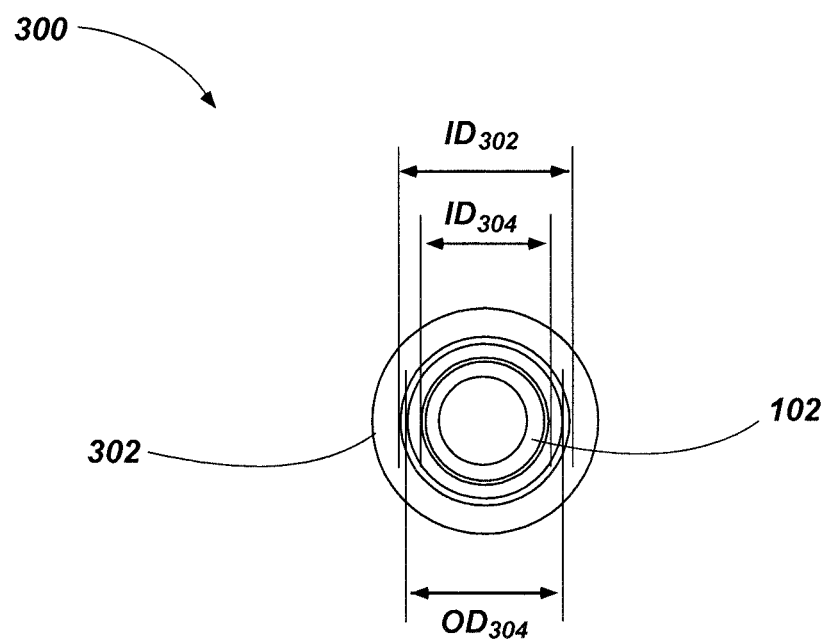
FIG. 6 depicts a cross-sectional view of a portion of the anchor deployment device shown in FIG. 4 with a medical device received in the anchor deployment device.

FIG. 6 depicts a cross-sectional view of a portion of the anchor deployment device 300 shown in FIG. 4 with the medical device 102 received in the anchor deployment device 300. As shown in FIG. 6, the inner diameter $ID_{304}$ of the anchor cannula 304 is sized to enable the medical device 102 to be received within the anchor cannula 304. The inner diameter $ID_{302}$ of the deployment cannula 302 may be greater than an outer dimension $OD_{304}$ of the anchor cannula 304 such that the anchor cannula 304 may be received and movable within the deployment cannula 302.

Figure 7:
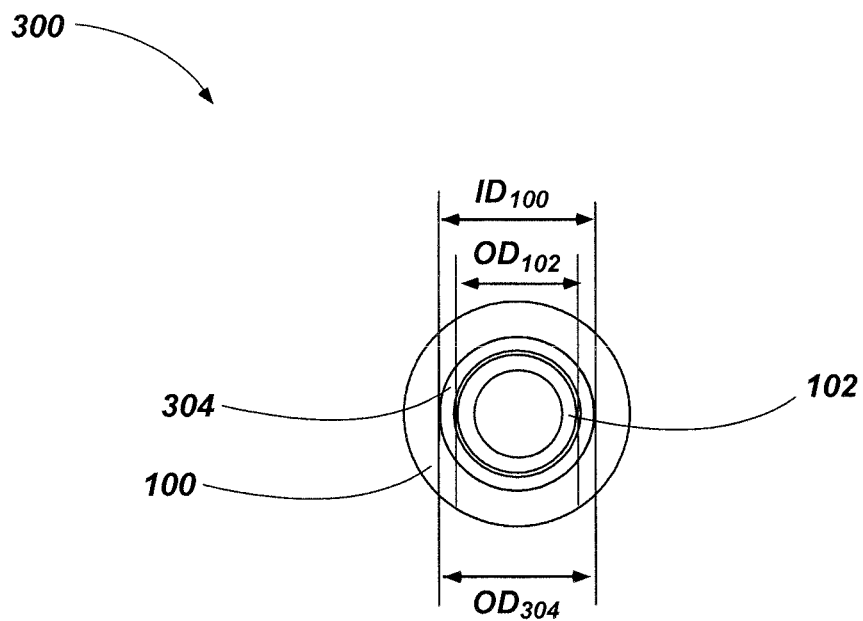
FIG. 7 depicts another cross-sectional view of a portion of the anchor deployment device shown in FIG. 4 with the medical device received in the anchor deployment device and an anchor element attached to the anchor deployment device.

FIG. 7 depicts another cross-sectional view of a portion of the anchor deployment device 300 shown in FIG. 4 with the medical device 102 received in the anchor deployment device 300 and the anchor element 100 attached to the anchor deployment device 300. The outer diameter $OD_{304}$ of the anchor cannula 304 may be greater than an inner diameter of the anchor element 100 such that the anchor cannula 304 acts to enlarge a cross-sectional area of the lumen formed within a portion of the anchor element 100 to form an enlarged inner diameter $ID_{100}$ of the anchor element 100 that is substantially equal to the outer diameter $OD_{304}$ of the anchor cannula 304. The enlarged inner diameter $ID_{100}$ of the anchor element 100 may be greater than an outer diameter $OD_{102}$ of the medical device 102 such that the enlarged inner diameter $ID_{100}$ of the anchor element 100 may be deployed over the outer diameter $OD_{102}$ of the medical device 102. When the anchor element 100 is removed from the anchor cannula 304 (e.g., by the deployment cannula 302 as discussed above), the anchor element 100 may contract toward the initial diameter to the anchor element 100 (e.g., where the initial diameter of the anchor element 100 is less than the outer diameter $OD_{102}$ of the medical device 102) in order to secure the anchor element 100 to the medical device 102.

Figure 8A:
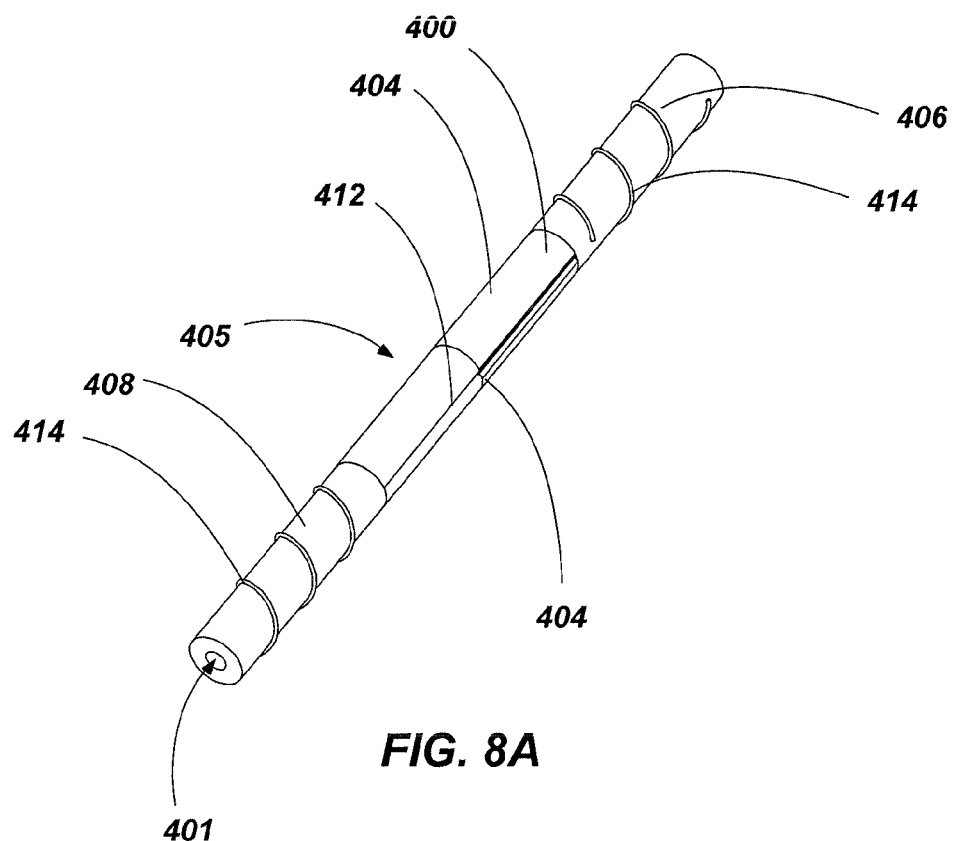
FIGS. 8A and 8B depict an anchor element in accordance with an embodiment hereof in an initial state and a deployed state, respectively.
Figure 8B:
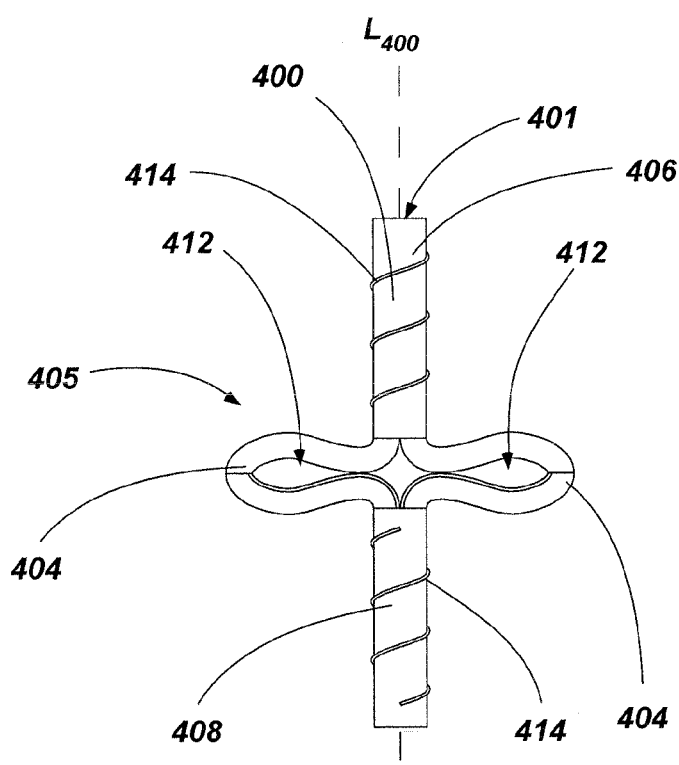

FIGS. 8A and 8B depict an anchor element 400 in an initial state and a deployed state, respectively. The anchor element 400 may be similar to and include one or more of the same features and functioning as the anchor elements 100, 200 discussed above with reference to FIGS. 1 through 3B. As shown in FIG. 8A, the anchor element 400 includes a lobe portion 405 positioned between the engagement portions 406, 408 of the anchor element 400. The body of the anchor element 400 may form a lumen 401 therein. Lobes 404 (e.g., two lobes) of the lobe portion 405 are formed about the anchor element 400 (e.g., at equal circumferential spacing) by slits 412 in the tubular body of the anchor element 400. In the initial state, the lobe portion 405 of the anchor element 400 is substantially parallel to (e.g., coextensive with) a longitudinal axis $L_{400}$ of the anchor element 400.

Referring also to FIG. 8B, the engagement portions 406, 408 may be moved toward each other to transition the anchor element 400 to the deployed state. The slits 412 enable the lobes 404 to extend outwardly (e.g., in a direction lateral or transverse (e.g., perpendicular) to the longitudinal axis $L_{400}$ of the anchor element 400) from a portion of the anchor element 400 (e.g., from the engagement portions 406, 408).

As depicted, the anchor element 400 may include a biasing feature (e.g., a radial biasing feature). For example, the anchor element 400 may include one or more springs 414 extending about at least a portion of the anchor element 400 (e.g., the engagement portions 406, 408). In some embodiments, the springs 414 are disposed on an exterior portion of the anchor element 400. In other embodiments, the springs 414 may be disposed within the anchor element 400. The springs 414 may act to bias the anchor element 400 in (e.g., toward) an initial state. For example, the springs 414 may act to radially bias the engagement portions 406, 408 of the anchor element 400 inward in a direction toward the lumen 401 (e.g., constricting the lumen 401) such that the springs 414 bias the engagement portions 406, 408 to or toward an initial state (e.g., an unstretched inner diameter of the anchor element 400). In some embodiments, the springs 414 act to relatively more rapidly tighten the anchor element 400 around a medical device 102 (see, e.g., FIG. 5).

It is noted that any anchor element disclosed herein (e.g., anchor elements 100, 200) may include a radial biasing feature (e.g., springs). In other embodiments, the anchor element may include an axial biasing feature.

Figure 9:
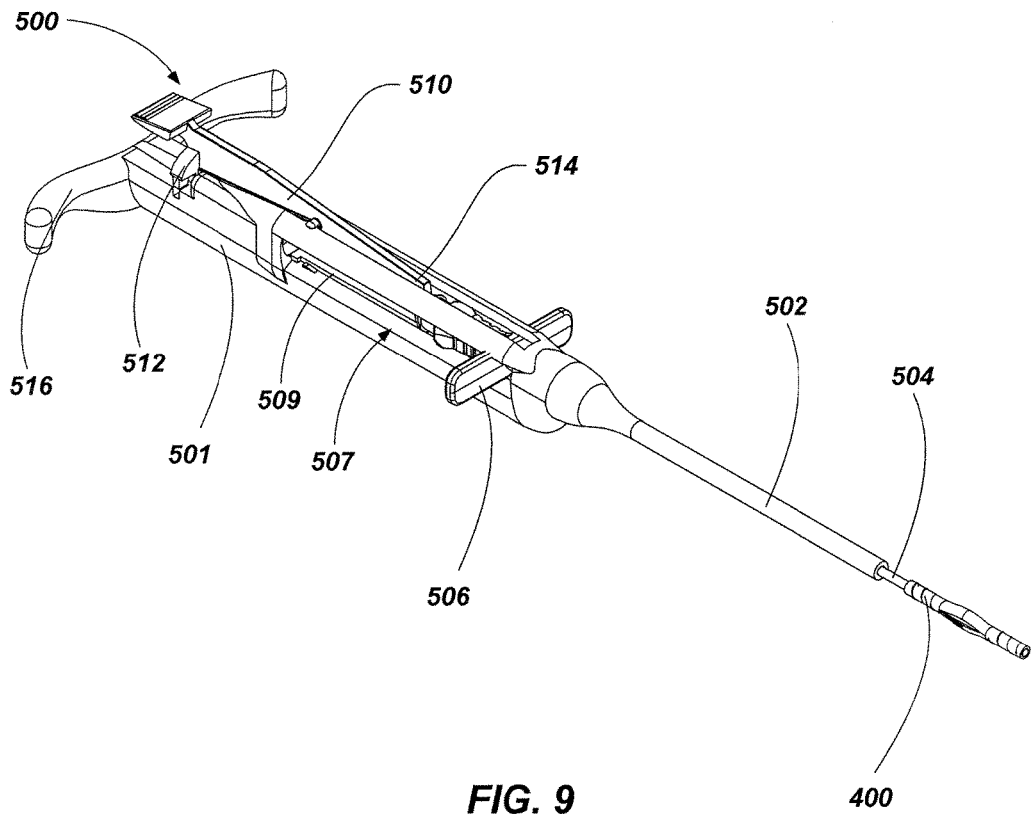
FIGS. 9 and 10 depict a perspective view and a side view, respectively, of an anchor deployment device in accordance with an embodiment of the disclosure.
Figure 10:
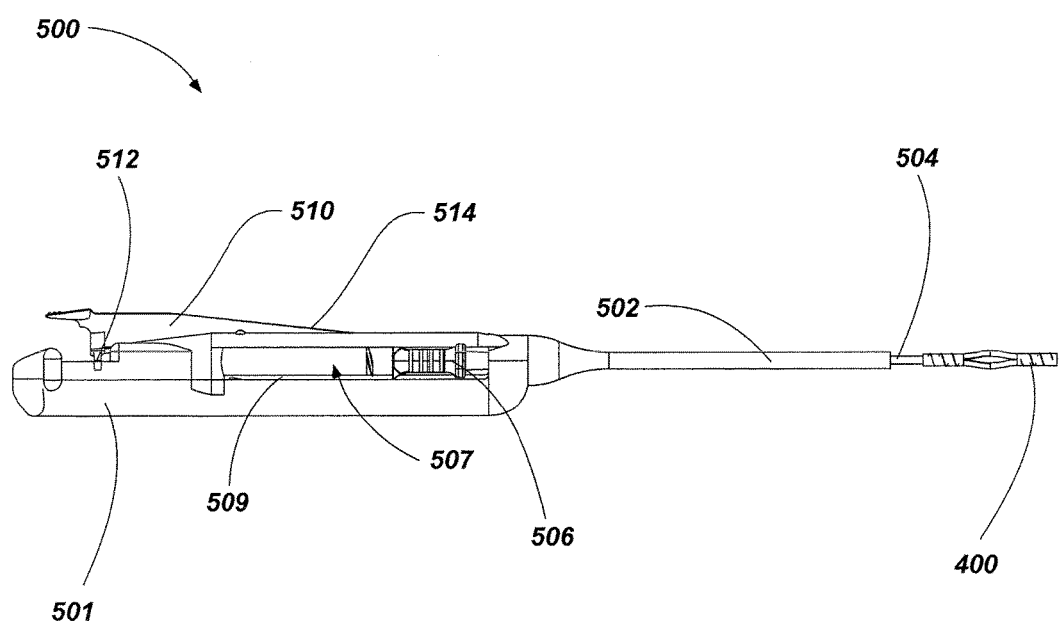

FIGS. 9 and 10 depict a perspective view and a side view, respectively, of an anchor deployment device 500. The anchor deployment device 500 may be similar to and include one or more of the same features and functioning as the anchor deployment device 300 discussed above with reference to FIGS. 4 through 7. As shown in FIGS. 9 and 10, the anchor deployment device 500 includes a first cannula (e.g., deployment cannula 502) and a second cannula (e.g., anchor cannula 504) received at least partially within the deployment cannula 502. The anchor deployment device 500 may include a handle 506 (e.g., formed as a hub) coupled to the anchor cannula 504 such that the handle 506 and the anchor cannula 504 may be moved relative to another portion of the anchor deployment device 500 (e.g., a body 501 of the anchor deployment device 500). For example, the body 501 of the anchor deployment device 500 may define an opening or chamber 507 in which the handle 506 is at least partially disposed. In some embodiments, the body 501 of the anchor deployment device 500 defines a track 509 in the chamber 507 upon which a portion of the handle 506 (e.g., a complementary portion) may move along (e.g., slide) to guide (e.g., and retain) the handle 506 and the anchor cannula 504 relative to the body 501 and the deployment cannula 502. Movement of the handle 506 relative to the body 501 enables a user (e.g., medical practitioner) to slide the anchor cannula 504 relative to the deployment cannula 502 along a common axis.

As depicted, the anchor deployment device 500 is shown with an anchor element (e.g., anchor element 400 in a distended state of the inner diameter) positioned on the anchor cannula 504 of the anchor deployment device 500. As above, the anchor deployment device 500 may have an inner dimension (e.g., diameter) that is sized to enable at least a portion of a medical device 102 (FIG. 5) to be received within the anchor cannula 504. As also described above, the handle 506, the anchor cannula 504, and the deployment cannula 502 may be utilized to deploy one or more anchor elements on a medical device (e.g., anchor elements 100, 200, 400 on medical device 102 as shown and described above).

As further depicted in FIGS. 9 and 10, the anchor deployment device 500 may include upper handle 510. A first end of upper handle 510 may include a locking mechanism 512 that holds (e.g., locks, clamps, etc.) the medical device 102 (FIG. 5). For example, the locking mechanism 512 may secure the medical device 102 when an anchor element is being deployed on the medical device 102 (e.g., when at least a portion of the medical device 102 is resident in a subject).

A second end of upper handle 510 may include a protrusion or elongated member 514 that engages with the handle 506 to secure the handle 506 and the anchor cannula 504. For example, the elongated member 514 of the upper handle 510 may retain the handle 506 and the anchor cannula 504 and prevent the handle 506 and the anchor cannula 504 from sliding relative to the body 501 of anchor deployment device 500.

The upper handle 510 may be configured such that the first end and the second end move (e.g., pivot) relative to each other. For example, when the locking mechanism 512 is securing the medical device 102 (FIG. 5), the elongated member 514 is disengaged with the handle 506, thereby enabling the handle 506 and the anchor cannula 504 to move relative to the body 501. Similarly, when the elongated member 514 is engaged with the handle 506 and restricting the handle 506 and the anchor cannula 504 from moving relative to the body 501, the locking mechanism 512 is disengaged from the medical device 102, thereby enabling the anchor deployment device 500 to move (e.g., slide) along the medical device 102. Such a configuration may enable the anchor deployment device 500 to be secured to the medical device 102 while an anchor element is being deployed and, likewise, secure the anchor deployment device 500 from any unwanted movement of the anchor cannula 504 relative to the deployment cannula 502 when the anchor deployment device 500 is being moved and positioned along the medical device 102.

The anchor deployment device 500 may include rear handle 516 that enables a user to move and position the anchor deployment device 500 along the medical device 102.

It is noted that to the extent that the anchor deployment devices are described in use with a particular anchor element, in other embodiments, the anchor deployment devices may be utilized with any suitable anchor element (e.g., anchor elements 100, 200, 400).

It is further noted that while the anchor elements and components of the anchor deployment device are primarily discussed herein as having a diameter, these elements are not necessarily limited to circular cross sections. For example, the anchor elements and components of the anchor deployment device, and the lumens formed therein, may have a square, circular, oval, rectangular, or any other suitable cross-sectional shape.

Referring to FIGS. 1 through 10, in operation, a lumen of an anchor element (e.g., lumen 101, 201, 401 of anchor element 100, 200, 400) is enlarged to position the anchor element 100, 200, 400 on the anchor cannula 304 of the anchor deployment device 300. A medical device 102 (e.g., a medical device that has already been inserted and positioned within a subject) is positioned within the anchor element 100 and the anchor deployment device 300 and anchor element 100, 200, 400 are moved along the medical device 102 to position the anchor element 100, 200, 400 within the subject. The anchor element 100, 200, 400 may then be deployed within the subject utilizing the handle 306 of the anchor deployment device 300 to deploy the lobes 104, 204, 404 of the anchor element 100, 200, 400 and to force the anchor element 100, 200, 400 onto (e.g., about, around) the medical device 102 with the deployment cannula 302. Constriction of the anchor element 100, 200, 400 about the medical device 102 as the anchor element 100, 200, 400 contracts toward the initial lumen size of the anchor element 100, 200, 400 acts to secure the anchor element 100, 200, 400 about the medical device 102 while both the anchor element 100, 200, 400 and the medical device 102 are positioned within the subject. For example, the anchor element 100, 200, 400 may contract to the initial size of the lumen 101, 201, 401 of the anchor element 100, 200, 400 or to a cross-sectional area between the initial size and the enlarged (e.g., deformed) size of the lumen 101, 201, 401 of the anchor element 100, 200, 400. In some embodiments, the constriction of the anchor element 100, 200, 400 may also constrict or compress a portion of the medical device 102 (e.g., a cannula).

Once the anchor element 100, 200, 400 is placed over the medical device 102 within the subject, the lobes 104, 204, 404 of the anchor element 100, 200, 400 may anchor the medical device 102 by engaging with one or more portions of the subject's tissue to at least partially retain the medical device 102 in a desired position within the subject.

Once being apprised of the instant disclosure, one of ordinary skill in the art will be able to make and use the devices and assemblies disclosed herein. For example, the anchor elements may be formed from a polymer (e.g., a polyurethane such as CARBOTHANE®) and springs may be formed from a metal material (e.g., 316 stainless steel).

What is claimed is:

1. An anchor element assembly comprising: at least one anchor element having a longitudinal axis, the at least one anchor element comprising: at least two engagement portions; at least one lobe section positioned between the at least two engagement portion, the at least one lobe section comprising at least one lobe configured to extend transversely from the longitudinal axis of the at least one anchor element when the at least one anchor element is in a deployed state, the at least one lobe comprising a first end and a second end each being coupled to one respective engagement portion of the at least two engagement portions, the at least one lobe having a middle section positioned between the first end and the second end along the longitudinal axis, the middle section configured to define a laterally outermost portion of the at least one lobe, taken in direction transverse to the longitudinal axis, when the at least one anchor element is in the deployed state, the first end and the second end being separated by the middle portion when the at least one anchor element is in an initial state in a direction along the longitudinal axis; and a lumen formed within the at least one anchor element configured to receive at least a portion of a medical device in the lumen, the at least one lobe portion being defined by at least one slot in the at least one lobe section extending from an outer surface of the at least one anchor element to the lumen; and an anchor deployment device comprising: a first cannula configured to receive the at least one anchor element thereon and to receive a portion of the medical device therein, wherein the first cannula is separate from the medical device to which the at least one anchor device is to be secured; and a second cannula having configured to have at least a portion of the first cannula received therein, wherein the first cannula is movable relative to the second cannula, and wherein the second cannula is configured to: force one of the at least two engagement portions of the at least one anchor element toward another of the at least two engagement portions in order to position the at least one anchor element in the deployed state while the at least one anchor element is positioned on the first cannula; and force the at least one anchor element in the deployed state off of the first cannula in order to secure the anchor deployment device to the at least a portion of the medical device that is positioned within a subject, wherein the anchor deployment device is configured to be removed from the subject and the medical device after the at least one anchor device has been secured, and wherein neither the anchor deployment device nor the first cannula is configured to be secured in the subject by the at least one anchor element.

2. The anchor element assembly of claim 1, wherein:
in a first locking position, the anchor deployment device is adapted to substantially prohibit movement of the first cannula relative to the second cannula in order to secure the anchor deployment device from unwanted movement of the first cannula relative to the second cannula when the anchor deployment device is being moved and positioned along the medical device; and
in a second locking position, the anchor deployment device is adapted to substantially prohibit movement of the medical device relative to the first cannula in order to move the first cannula relative to the second cannula to enable the second cannula to force the at least one anchor element into the deployed state and onto the medical device.

3. The anchor element assembly of claim 1, wherein the first cannula is coupled to a hub movably received within a portion of the anchor deployment device such that movement of the hub translates the first cannula relative to the second cannula.

4. The anchor element assembly of claim 3, wherein the anchor deployment device further comprises a securing member configured to secure the hub to the anchor deployment device to prevent movement of the hub and the first cannula relative to the second cannula.

5. The anchor element assembly of claim 1, wherein the anchor deployment device further comprises a locking mechanism configured to secure the medical device to the anchor deployment device.

6. The anchor element assembly of claim 5, wherein the anchor deployment device further comprises a pivoting handle having the locking mechanism on a first side of the pivoting handle and a securing member on a second side of the pivoting handle, wherein, in a first position of the pivoting handle, the locking mechanism is configured to be engaged with the medical device and disengaged from a portion of a first cannula configured to receive the at least one anchor element thereon and, in a second position of the pivoting handle, the locking mechanism is configured to be disengaged from the medical device and engaged with the portion of the first cannula.

7. The anchor element assembly of claim 1, wherein an outer dimension of the first cannula of the anchor deployment device is greater than an inner dimension of the at least one anchor element, the first cannula configured to at least partially enlarge the lumen of the at least one anchor element in order to deploy the at least one anchor element over the at least a portion of the medical device.

8. The anchor element assembly of claim 3, wherein an inner dimension of the first cannula of the anchor deployment device is greater than an outer dimension of the at least a portion of the medical device, and wherein the first cannula is configured to receive the at least a portion of the medical device within a lumen formed within the first cannula.

9. The anchor element assembly of claim 1, wherein the anchor deployment device comprises a handle for moving the first cannula along the second cannula.

10. The anchor element assembly of claim 1, wherein the anchor deployment device is configured to at least partially move the at least one anchor element from the initial state where the at least one lobe section of the at least one anchor element is substantially parallel to the longitudinal axis of the at least one anchor element to the deployed state where the at least one lobe of the at least one lobe section extends transversely from the longitudinal axis of the at least one anchor element.

11. The anchor element assembly of claim 1, wherein the lumen of the at least one anchor element is configured to contract around the at least a portion of the medical device in order to secure the at least one anchor element to the at least a portion of the medical device.

12. The anchor element assembly of claim 11, wherein the at least one anchor element is configured to be secured to the at least a portion of the medical device via mechanical interference without the use of an adhesive or a fastener.

13. The anchor element assembly of claim 1, wherein the at least one lobe of the at least one anchor element comprises at least two lobes.

14. The anchor element assembly of claim 1, wherein the at least one lobe section of the at least one anchor element comprises at least two lobe sections spaced along the longitudinal axis of the at least one anchor element, each lobe section of the at least two lobe sections comprising at least two lobes.

15. The anchor element assembly of claim 14, wherein the at least two lobes of a first lobe section of the at least two lobe sections are offset about the longitudinal axis of the at least one anchor element from the at least two lobes of a second lobe section of the at least two lobe sections.

16. The anchor element assembly of claim 1, wherein the anchor deployment device is configured to secure the at least one anchor element over the at least a portion of the medical device while the at least a portion of the medical device is positioned within a subject.

17. The anchor element assembly of claim 1, wherein an outer dimension of the at least one cannula of the anchor deployment device is greater than an inner dimension of the at least one anchor element, the at least one cannula configured to at least partially enlarge the lumen of the at least one anchor element in order to deploy the at least one anchor element over the at least a portion of the medical device.

18. A medical device assembly comprising:
  a medical device configured to have at least a portion thereof positioned within subcutaneous tissue of a subject; and
  the anchor element assembly of claim 1 configured to secure the portion of the medical device within the subject.

19. A method of anchoring a medical device, the method comprising:
  positioning at least a portion of the medical device in a subject;
  positioning a lumen of at least one anchor element around a first portion of an anchor deployment device that is separate from and movable relative to the medical device;
  deploying at least two protrusions of the at least one anchor element to extend transversely from a longitudinal axis of the at least one anchor element while the at least a portion of the medical device is positioned within the subject with a second portion of the anchor deployment device while to the at least one anchor element remains positioned around the first portion of the anchor deployment device, each of the at least two protrusions defined by a middle portion the at least one anchor element that defines the lumen when the at least one anchor element is in an initial state and defines a laterally outermost portion of the at least one anchor element when the at least one anchor element is in a deployed state; and
  securing the at least a portion of the medical device within the lumen of the at least one anchor element by forcing the at least one anchor element off of the first portion of the anchor deployment device in the deployed state with the second portion of the anchor deployment device.

20. The method according to claim 19, further comprising:
  enlarging the lumen of the at least one anchor element with the anchor deployment device; and
  forcing the at least one anchor element off of the anchor deployment device to constrict the lumen of the at least one anchor element about the at least a portion of the medical device.

* * * * *